United States Patent [19]

Levitt

[11] Patent Number: 4,911,706

[45] Date of Patent: Mar. 27, 1990

[54] AUTOMATIC NEEDLE COVER

[75] Inventor: Michael D. Levitt, Minneapolis, Minn.

[73] Assignee: Regents of the University of Minnesota, Minneapolis, Minn.

[21] Appl. No.: 258,199

[22] Filed: Oct. 14, 1988

[51] Int. Cl.$^4$ .............................................. A61M 5/32
[52] U.S. Cl. .................................... 604/198; 604/263
[58] Field of Search ............... 604/110, 117, 162, 192, 604/198, 263

[56] References Cited

U.S. PATENT DOCUMENTS

| | | | |
|---|---|---|---|
| 1,436,707 | 11/1922 | Gashke | 604/117 |
| 4,735,618 | 4/1988 | Hagen | 604/110 X |
| 4,790,828 | 12/1988 | Dombrowski et al. | 604/263 X |

Primary Examiner—Dalton L. Truluck

Attorney, Agent, or Firm—Kinney & Lange

[57] ABSTRACT

An automatic needle cover is mounted onto the base of a hypodermic needle on a syringe and leaves the needle exposed for initial use, such as for withdrawing blood or the like. A releasable tab is either cut or released, and a resilient support arm pushes a protective cap out past the end of the needle, to cover the end of the needle and prevent an accidental pricking of the user's skin. The contents of the syringe can drip freely out of the cap, or if desired, the cap can be braced against a depression in a rubber stopper of a container, to thereby facilitate realigning the hole in the cap with the needle, so that the needle contents can be discharged into the container. The protective cap is made so that it moves laterally to insure covering the point of the needle so that the point will not accidentally protrude.

6 Claims, 2 Drawing Sheets

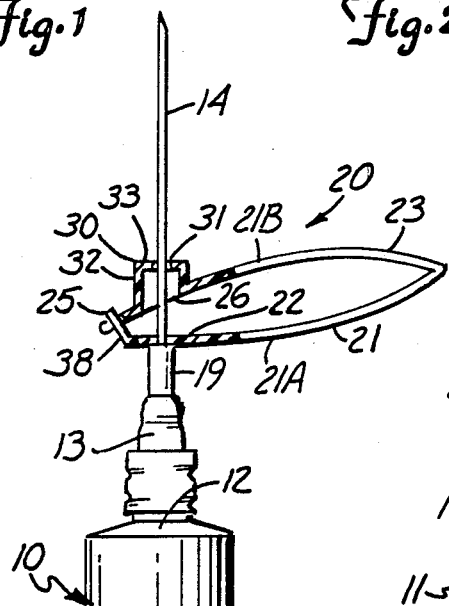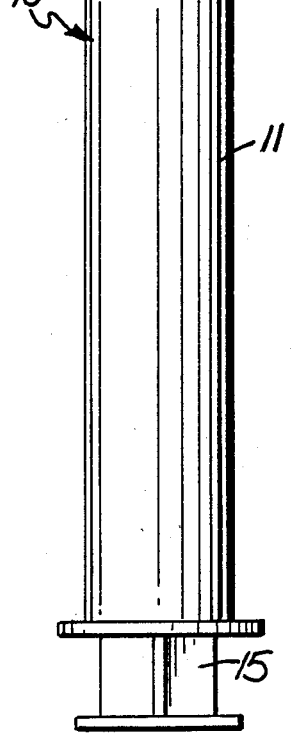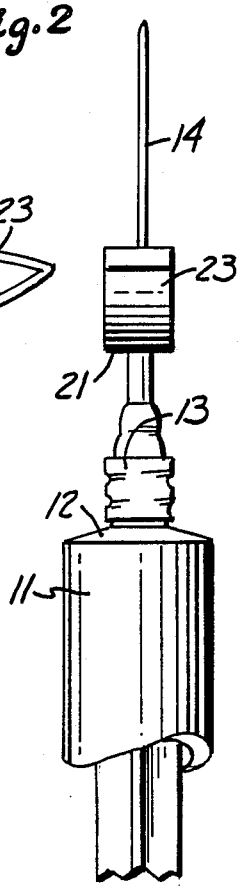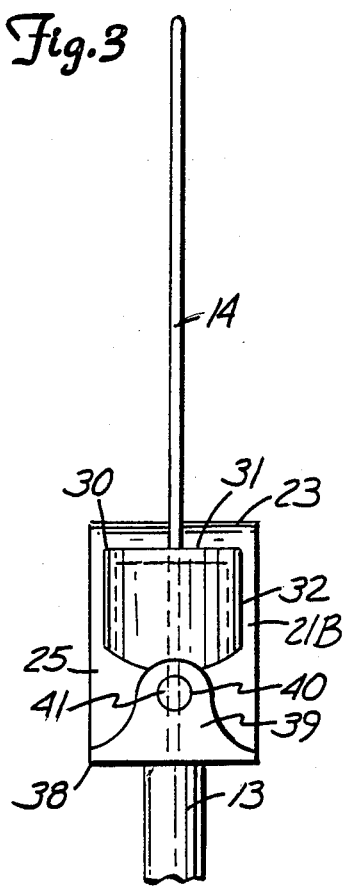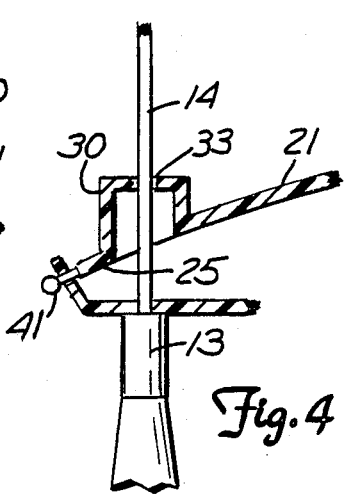

AUTOMATIC NEEDLE COVER

BACKGROUND OF THE INVENTION

1. Field of the Invention.

The present invention relates to protectors for the points of needles used on hypodermic syringes.

2. Description of the Prior Art.

In the prior art, various needle protectors have been advanced. U.S. Pat. No. 4,725,267 discloses a needle sheath that moves forward over the needle tip on a sleeve. An end cap tilts when the sheath or cap carrying support is extended so the needle tip engages a corner of the cap for protecting the tip against causing a scratch. The tilting cap is carried by a spring or accordion pleated tube which extends along the length of the needle under the spring load when the needle protection is actuated.

U.S. Pat. No. 4,139,009 shows a needle assembly with a retractable needle cover, that extends over the point of the needle and which must be slid out of the way when the needle is to be used. The needle opening in the cover is always aligned with the needle, so that any retracting force on the cover will cause the cover to move back and the needle point will be exposed so that it can puncture or scratch a finger accidentally. Thus, the cover does not adequately protect against an accidental scratching.

U.S. Pat. No. 4,693,708 shows a needle guard device incorporated into a syringe assembly which includes a sleeve or shield that can be locked in position to provide coverage when extended out over the needle. The sleeve can be locked in place.

U.S. Pat. No. 4,747,837 also discloses a slidable cover on a syringe body that can be extended and latched to cover the needle point after the syringe has been used. A large sleeve covers the needle, and it has an opening at its outer end adjacent the needle tip. If the sleeve becomes unlatched, the needle would easily be exposed.

U.S. Pat. No. 4,758,231 discloses a casing for a syringe assembly that can be pulled out over the needle after use and has locking ribs to hold the cover extended, but if the locks are dislodged the needle easily slides out through the opening in the end of the sleeve that is used for protection. The latches used for holding the shield in the outer position, can be any one of a number of different latches. A full-length tubular member is necessary, which is quite large, and requires positive manual operation.

The activity of the prior art shows the need for a simple, low cost and easily operated needle guard that will provide for safety against accidental scratching or puncturing of the skin.

SUMMARY OF THE INVENTION

The present invention relates to an automatic protective device for a hypodermic needle and syringe. A resilient (spring loaded) folding support arm is attached (preferably integrally molded) to the hub of the needle and carries an inverted cuplike cap which includes a base or end wall having an opening through which the needle initially extends. The arm and cap are made to be easily released without any manipulation once the sterile package is opened and the hypodermic needle is removed. The cap and arm can be made separate from the needle base and held in place with a friction fit.

The needle can be inserted into a vein and blood drawn, and while the needle is still i position, a tear away tab or other release latch (including a cutting of the retainer) can be maneuvered with one hand to release the latch or retainer and the cap. When the needle is withdrawn, the inverted cap will slide out along the needle because of the spring loading from the folded support arm. The cap end or base wall member is joined along a circumscribing corner to a cylindrical side wall. The end wall is formed at a slant relative to the outer end portion of the folding arm. When the base wall of the cap is extended out beyond the end of the needle, the needle tip slips into the interior of the cap and the cap moves sideways so the needle slips over to the corner of the cap where the end wall and side wall join. The needle is then offset from the opening in the end wall of the cap and is protected by the side and end walls of the cap from accidentally scratching or sticking a finger. In this position, the support arm and cap have to be positively manipulated in order to realign the hole in the cap with the needle point. The hole in the base or end wall of the cap is a relatively loose fit around the needle so it can be easily manipulated.

Thus, protection against accidental exposure of the needle end is achieved. Manipulation can be done by placing the end of a container that has an outer cover on it and in which the blood sample in the syringe (or other syringe contents) is to be injected, such as a rubber stopper vial sold under the trademark Vacutainer against the cap and then moving the syringe and needle. The realignment is easily and positively done so that the needle can be exposed and inserted through the stopper to discharge the syringe contents into the vial.

When the cap is braced against a resilient structure such as a rubber stopper of a bottle or tube, the hole in the cap can be realigned without touching either the needle or the cap with the fingers. The user can see the entire length of the needle because the assembly is very short axially. This helps in insertion into a patient. The arm and cap are made so that the needle tip will be automatically covered without further manipulation upon removal of the needle from the skin after use.

The inverted cup that is used as a protector has to have a cover forming end wall that extends transversely of the needle and which shifts over the point of the needle when the needle slips out of the normal hole through which the needle extends. The folding support arm moves in an arc and tends to tilt the end cap as it extends so there is misalignment of the needle and the needle opening in the end cap at the extended position of the cap. The needle then will not accidentally slide through the hole.

The protector can easily be molded, and simply attached to the needle hub or support at the base of the syringe in a number of ways. The cap also can be separately made and loosely attached to the support arm.

BRIEF DESCRIPTION OF THE DRAWINGS

FIG. 1 is a side elevational view of a hypodermic syringe having a needle guard made according to the present invention installed thereon;

FIG. 2 is an enlarged side elevation view showing the latching mechanism used with the present invention;

FIG. 3 is a view of the syringe of FIG. 1 from an opposite end from FIG. 2;

FIG. 4 is an enlarged fragmentary vertical sectional view taken as on line 3—3 in FIG. 4;

FIG. 5 is a sectional view showing the needle guard of the present invention extended out over the needle;

DETAILED DESCRIPTION OF THE PREFERRED EMBODIMENTS

Figure 6:
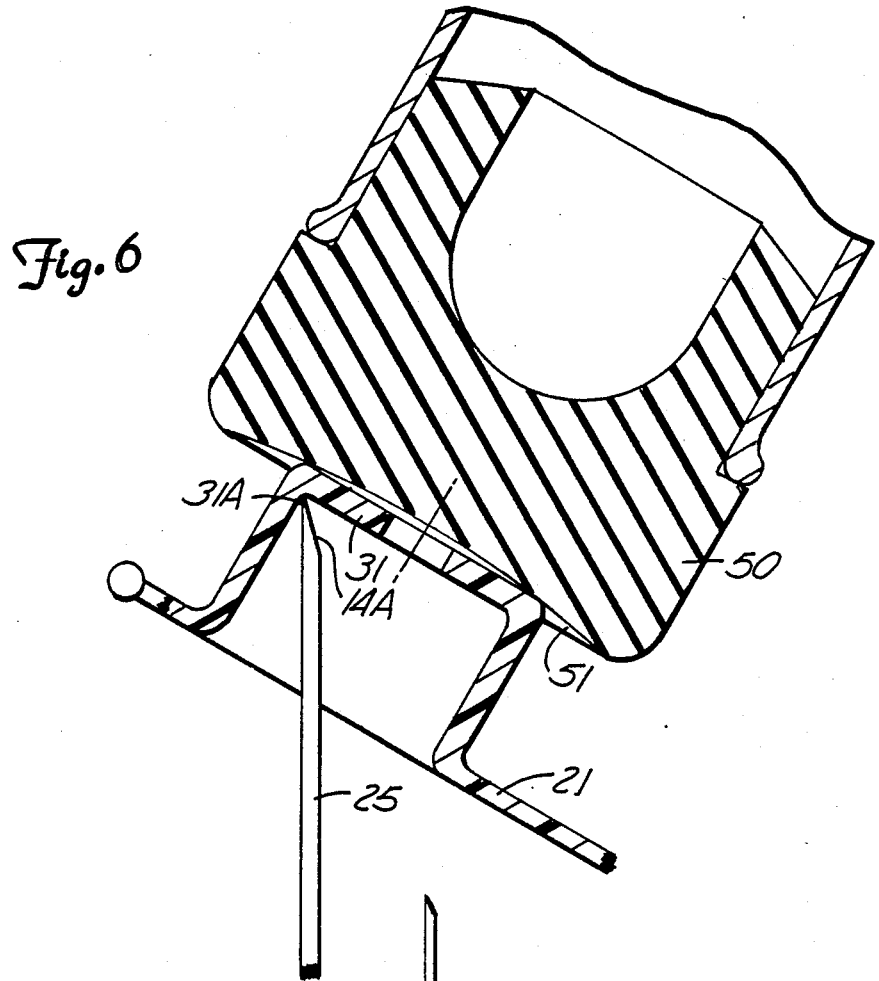
FIG. 6 is an enlarged view showing the needle cap protecting the point, and in place against the rubber stopper of a container into which the syringe contents are to be discharged.

A hypodermic syringe indicated generally at 10 comprises a standard cylindrical barrel 11 which may be formed of a transparent plastic, and which is a hollow cylinder having an end wall portion 12 on which a needle attaching sleeve 13 of suitable design is mounted. The needle attaching sleeve 13 can be molded to the barrel at the time of manufacture, and suitable means of any desired type can be made to support the hypodermic needle 14 at the outer end of the needle attaching sleeve. A syringe plunger 15 has a piston member on the interior of the barrel 11 and can be slid outwardly along the interior of the barrel to draw fluids or blood in through the hypodermic needle 14 (which has a sharp, open point). The plunger also can be moved inwardly to discharge the barrel contents through the needle.

A needle guard assembly indicated generally at 20 is shown installed on the molded hub 19 of the needle, adjacent the needle attaching sleeve 13, and can be attached to the needle in any suitable way; preferably it will be molded in place. The guard assembly also can be cemented or frictionally attached in place. The needle guard assembly comprises a resilient or spring loaded folding support arm 21 that has a base end 22 which is the portion of the guard attached to the needle hub in a suitable manner. The arm 21 includes a spring loaded elbow type hinge joint 23 approximately midway between the base end 22 and an outer end 25. The elbow hinge divides the arm into too arm sections 21A and 21B. The intermediate ends of the arm sections 21A and 21B are joined together at the elbow joint 23. The arm outer end 25, as shown, has an opening 26 therein of a size to permit the needle 14 to slide therethrough.

The outer end 25 of the arm 21 has an inverted cup-like cap 30 molded thereon, and as shown, the cap 30 has a base or end wall 31 and a generally cylindrical outer side wall 32 circumscribing the end wall and molded integrally with the end wall at a corner junction. The side wall 32 is formed so that the end wall 31 defines a lane that is inclined with respect to he general plane of the arm section 21B at outer end portion 25. The cap more or less "cants" in relation to the outer end 25 of the arm 21.

The end wall 31 has a central or axial opening 33 through which the needle 14 can extend, and as shown when the arm 21 is folded or retracted as seen in FIG. 1, the needle 14 passes through both the opening 26 and the opening 33. The outer end 25 of the arm defines a plane support member that is inclined with respect to the central axis of the needle in retracted position, and when in released position, the outer arm section 21B moves in an arc outwardly and the outer end portion 25 inclines relative to the axis of needle. The arm section extends outwardly from the needle and inclines in direction back toward the barrel 11.

The outer end 25 of the arm 21 is retained in a retracted position with respect to the base portion 22 against the arm resilient force (or spring load at hinge 25) tending to urge the outer end 25 toward the outer end of the needle through a suitable cuttable or releasable latch or retainer indicated at 38. As shown, the retainer 38 can be a tear away tab or ear made with a weakened junction for tearing it away, much like the tabs on plastic milk bottle caps. If desired, the latch can be a molded ear 39 (see FIG. 3), which has an aperture 40 that fits over a small projection or knob 41 which is molded onto the outer end 25 of the arm 21. The latch should be low cost and simple to operate. It can be any desired type.

The outer (sharpened) end or point 14A of the needle 14 can be inserted into a patient, with the needle protector in retracted position as shown in FIG. 1. The length of needle 14 exposed beyond the base wall 31 of the cap 30 is sufficient so that it can be inserted into an arm to withdraw blood from a vein, for example. The plunger 15 will be drawn out, so that the blood sample will be taken from the arm, and before the needle 14 is removed, the latch assembly 38 or tear away strip will be released, or cut, and the resilient springlike plastic material forming a spring load at hinge 23 creates a force which tends to unfold the arm sections 21A and 21B causing the outer end 25 of the arm to slide along the length of the needle 14 toward the outer tip 14A. When the base wall 31 of the cap extends beyond point 14A, the needle tip retracts inwardly of the base wall 31, and the angle of the axes of the opening 33 and the arc or path of movement of the arm section 21B will be such that the needle tip 14A will be urged over toward a corner or junction of the walls 30 and 32 of the cap 30, along the longer side of the side wall 32, as shown in FIG. 5. The needle tip 14A then will rest along the side wall 32 at the corner 32A where the side wall 32 joins the base wall 33, and the opening 33 will be off to the side of the needle.

The outer end portion 25 of the arm section 21B forms an inclined plane positioned at an angle with respect to the needle axis that is substantially equal to but inclined in opposite direction from the angle of the arm section 21B when in its retracted position. This means that the needle tip 14A will be fully protected and will not b accidentally exposed for scratching or pricking the skin of a person. The protective cap will remain in place automatically, but when one wants to place the blood sample or other contents of the syringe into a container that has a rubber cap or stopper indicated at 50 (FIG. 6), the base wall 31 of the cap can be braced against a concave surface 51 of the stopper and then he cap slid over so that the needle tip 14A passes through the opening 33. The needle 14 then can be pushed through the rubber cap 50 and the syringe contents discharged into the container.

The cap member can be molded in place along with the folding arm 21, and the openings 26 and 33 for the needle also can be molded so that they are aligned. These openings are of size to provide clearance. The plane of the base wall 33 is canted with respect to the general plane of the arm section on which it is mounted. The axes of the holes 33 and the hole 26 are not aligned, as shown in FIG. 5 but rather are at a desired angle so that when the plane of the arm outer end portion 25 inclines with respect to the needle as the arm moves outwardly, the opening 33 will move off to the side of the needle and the needle point 14A will rest in the corner of the cap.

The cap can have drain openings molded through the side wall adjacent to the region where it attaches to the support arm. This will help in seeing drips from the needle tip. Also, the cap can be molded separately and attached to the arm in a suitable manner.

Figure 7:
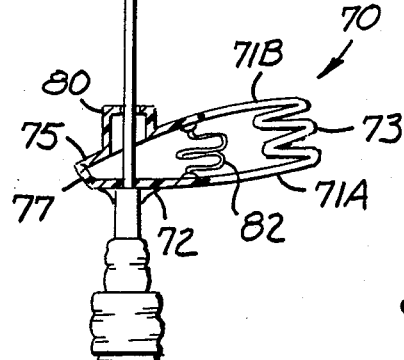
FIG. 7 is a side elevational view similar to FIG. 2 of a modified form of the invention.

In FIG. 7, a modified needle guard assembly 70 is shown. In this form, a support arm 71 has a base end 72, which can be mounted on a needle hub in a suitable manner. A bellows type or accordian folded spring hinge joint 73 joins two arm sections 71A and 71B which are joined by the joint 73. The arm 71, as molded, has an outer end 75 which is folded back against the base end 72 and is originally retained with a short tear-away strip 77 that has a break or tear line on both the upper and lower sections of the arm.

The arm section 71B has a cap 80 on its outer end which fits over the needle as explained before.

The accordian spring connector or joint 73 urges the cap 80 outwardly on the needle so when the guard is to be used, strip 77 is pulled away or cut and the arm section 71B will spring outwardly.

The cap will cover the needle point as previously explained to protect the user.

A tether cord or line 82 can be molded in place between the arm sections 71A and 71B, or added as a separate line after molding. The tether cord is used as a stop to stop extension of the arm section 71B and cap 80 at the desired position. The cord prevents the arm section 71 from sliding all the way off the needle.

The action of the cap is as previously explained for protection.

The protective device thus is fairly simple, and uses a folding spring loaded arm which is held with external fasteners in a retracted position until the protective device is to be used (after the needle has been used). Then the latch is released and the arm will automatically spring out to cover the needle point. If desired, the arm 21 can be retained in its maximum outward position with suitable latch members. The arm can be made so that it will only extend out to the correct position and will not extend beyond the needle tip. The arm 21 can be made in sections and separately spring loaded so the outer arm section moves outwardly if desired. Note also that the contents of the syringe can drip freely out of the cap when the needle is held upright.

Although the present invention has been described with reference to preferred embodiments, workers skilled in the art will recognize that changes may be made in form and detail without departing from the spirit and scope of the invention.

What is claimed is:

1. A needle protection device comprising a folding, spring loaded arm, said arm having a base end and an outer end, and being folded upon itself in the center the spring load urging the arm to unfold to move the outer end away from the base end;
   means for mounting said base end in position adjacent the base of a hypodermic needle;
   said outer end having an opening therethrough;
   means to releasably latch said arm in a retracted position wherein the outer end of the arm is retained near the base end, against the spring load on the arm urging the outer end outwardly; and
   a cap member mounted on said outer end of the arm, said cap having a base wall, and a substantially circumscribing wall around the base wall defining an interior, the circumscribing wall being attached to said outer end of said arm on a side of the end opposite from the arm base when the arm is in a folded position, the outer end of said arm being urged outwardly such that upon release of the latch the cap slides along the length of the needle to a second position, the cap being mounted so that when the base wall of the cap clears the needle tip the base wall is urged to move the opening through the cap base wall laterally so that the point of the needle engages the side wall and base wall junction region on the cap member interior.

2. The apparatus as specified in claim 1 wherein said arm forms a generally flat strap, said strap being divided into inner and outer sections by folding in the center, the outer section having a surface inclined with respect to a central axis of the needle with the arm in retracted position, the base wall of said cap also being inclined with respect to said surface.

3. The apparatus as specified in claim 2 wherein said surface of said outer end section inclines with respect to the needle axis in an opposite direction when it is in its second position from the direction of inclination of the outer end section when the arm is folded and in its retracted position.

4. The apparatus as specified in claim 3 wherein the base wall of the cap is urged laterally by pivoting movement of the arm as the arm moves to a second position.

5. The apparatus of claim 1 and means for providing spring loading of the outer end of the arm comprising an accordian pleated spring member dividing the folded arms into inner an outer sections.

6. A needle protection device comprising a folding, spring loaded arm means, said arm means having a base end and an outer end, and being folded upon itself in the center portions thereof, the spring load urging the arm means to unfold to move the outer end away from the base end;
   means for mounting said base end in position adjacent the base of a hypodermic needle;
   means to releasably latch said arm means in a retracted position wherein the outer end of the arm means is retained near the base end, against the spring load on the arm means urging the outer end outwardly; and
   a cap member mounted on said outer end of the arm, said cap members having a base wall, and a substantially circumscribing wall around the base wall defining an interior, the circumscribing wall being attached to said outer end the base end of the arm means and the base wall of the cap having openings therein so that when mounted with a hypodermic needle and the arm means in folded position such needle extends through the openings and is substantially fully exposed, said arm being urged outwardly such that upon release of the lateral means the cap slides along the length of the needle to a second position with the base wall of the cap covering a tip of such hypodermic needle.

* * * * *

UNITED STATES PATENT AND TRADEMARK OFFICE
CERTIFICATE OF CORRECTION

PATENT NO. : 4,911,706
DATED : March 27, 1990
INVENTOR(S) : Michael D. Levitt

It is certified that error appears in the above-identified patent and that said Letters Patent is hereby corrected as shown below:

In the References Cited Section, under U.S. PATENT DOCUMENTS, add the following:

| | | | |
|---|---|---|---|
| 4,139,009 | 2/1979 | Alvarez | 128/218 |
| 4,693,708 | 9/1987 | Wanderer et al | 604/198 |
| 4,725,267 | 2/1988 | Vaillancourt | 604/192 |
| 4,747,837 | 5/1988 | Hauck | 604/198 |
| 4,758,231 | 7/1988 | Haber et al | 604/198 |

Column 6, line 27, delete "claim 3", insert --claim 2--.

Signed and Sealed this

Second Day of July, 1991

Attest:

HARRY F. MANBECK, JR.

Attesting Officer     Commissioner of Patents and Trademarks